United States Patent
Kobayashi et al.

[11] Patent Number: 5,928,660
[45] Date of Patent: Jul. 27, 1999

[54] COSMETIC RAW MATERIAL, A COSMETIC PRODUCT AND A METHOD OF MANUFACTURING A COSMETIC PRODUCT

[75] Inventors: Kazuo Kobayashi; Hidetoshi Kondo; Yoshitsugu Morita; Ryuji Tachibana, all of Chiba Prefecture, Japan

[73] Assignee: Dow Corning Toray Silicone Co., LTD., Tokyo, Japan

[21] Appl. No.: 09/109,809

[22] Filed: Jul. 2, 1998

[51] Int. Cl.$^6$ ............................. A61K 6/00; A61K 7/00; A61K 7/035
[52] U.S. Cl. ............................. 424/401; 424/69; 514/844
[58] Field of Search ...................... 424/401, 69; 514/844

[56] References Cited

FOREIGN PATENT DOCUMENTS 520 466 A2  12/1992  European Pat. Off. .

*Primary Examiner*—Thurman K. Page
*Assistant Examiner*—Sharon Howard
*Attorney, Agent, or Firm*—James L. De Cesare

[57] ABSTRACT

The object of the present invention is to provide [a] a cosmetic raw material which allows the uniform dispersion of a powdered silicone rubber in a cosmetic, [b] a cosmetic [i] which consists of the abovementioned cosmetic raw material and other cosmetic raw materials, [ii] which contains a uniformly dispersed powdered silicone rubber, and [iii] which has a good feeling on the fingers and skin, good spreading characteristics and a good feeling during use, and [c] a method for manufacturing such a cosmetic with good efficiency.

The present invention provides [a] a cosmetic raw material which is characterized by the fact that said material consists of an aqueous suspension of a powdered silicone rubber with a mean particle size of 0.1 to 500 microns, [b] a cosmetic which is characterized by the fact that said cosmetic consists of the abovementioned cosmetic material and other cosmetic materials, and [c] a cosmetic manufacturing method which is characterized by the fact that the abovementioned cosmetic raw material is mixed with other cosmetic raw materials.

6 Claims, No Drawings

COSMETIC RAW MATERIAL, A COSMETIC PRODUCT AND A METHOD OF MANUFACTURING A COSMETIC PRODUCT

DETAILED DESCRIPTION OF THE INVENTION

1. Technical Field of the Invention

The present invention concerns a cosmetic raw material, a cosmetic and a cosmetic manufacturing method. More specifically, the present invention concerns [a] a cosmetic raw material which allows the uniform dispersion of a powdered silicone rubber in a cosmetic, [b] a cosmetic [i] which consists of the abovementioned cosmetic raw material and other cosmetic raw materials, [ii] which contains a uniformly dispersed powdered silicone rubber, and [iii] which has a good feeling on the fingers and skin, good spreading characteristics and a good feeling during use, and [c] a method for manufacturing such a cosmetic with good efficiency.

2. Prior Art

The use of powdered silicone rubber as a cosmetic raw material for the purpose of improving the feeling and smooth applicability of cosmetics on the skin is universally known (see Japanese Patent Application Kokai No. 61-194009, Japanese Patent Application Kokai No. 2-243612, Japanese Patent Application Kokai No. 6-1709, Japanese Patent Application Kokai No. 8-12524, Japanese Patent Application Kokai No. 8-12545 and Japanese Patent Application Kokai No. 8-12546). Furthermore, it is known that powdered silicone rubbers with lower hardness values produce a greater improvement in the feeling during use of cosmetics containing such powdered silicone rubbers. Generally, the method used to mix powdered silicone rubbers with cosmetics is a method in which such powdered silicone rubbers are mixed together with other cosmetic raw materials. However, powdered silicone rubbers have a large cohesive force, and this cohesive force increases with decreasing hardness; accordingly, it is difficult to disperse such powdered silicone rubbers uniformly in cosmetics. This problem has been especially conspicuous in the case of liquid-form cosmetics, in which a sufficient shear force cannot be applied during the manufacture of the cosmetics. Furthermore, the following problem has also arisen: i.e., powdered silicone rubbers which are not uniformly dispersed in cosmetics harden the [tactile] feeling of the cosmetics, and thus cause a deterioration in the feeling of such cosmetics during use.

Problems Which the Present Invention Attempts to Solve

The present inventors conducted diligent research concerning the abovementioned problems, and arrived at the present invention as a result of this research. Specifically, the object of the present invention is to provide [a] a cosmetic raw material which allows the uniform dispersion of a powdered silicone rubber in a cosmetic, [b] a cosmetic [i] which consists of the abovementioned cosmetic raw material and other cosmetic raw materials, [ii] which contains a uniformly dispersed powdered silicone rubber, and [iii] which has a good feeling on the fingers and skin, good spreading characteristics and a good feeling during use, and [c] a method for manufacturing such a cosmetic with good efficiency.

Means Used to Solve the Abovementioned Problems

The cosmetic raw material of the present invention is characterized by the fact that said material consists of an aqueous suspension of a powdered silicone rubber with a mean particle size of 0.1 to 500 microns.

Furthermore, the cosmetic of the present invention is characterized by the fact that said cosmetic consists of the abovementioned cosmetic material and other cosmetic materials. Moreover, the cosmetic manufacturing method of the present invention is characterized by the fact that the abovementioned cosmetic raw material is mixed with other cosmetic raw materials.

Working Configurations of the Invention

First, the cosmetic raw material of the present invention will be described in detail. The cosmetic raw material of the present invention is characterized by the fact that said material consists of an aqueous suspension of a powdered silicon rubber. This aqueous suspension may be a liquid-form, creme-form or paste-form suspension, etc. The mean particle size of this powdered silicone rubber is in the range of 0.1 to 50 microns, and is preferably in the range of 0.5 to 50 microns. The reason for this is that cosmetics containing powdered silicon rubbers whose mean particle sizes are outside this range tend to be inadequate in terms of the feeling of the cosmetic on the fingers and skin, the spreading characteristics of the cosmetic and the feeling of the cosmetic during use. The shape of the powdered silicone rubber particles may be spherical, flat or amorphous; in particular, spherical particles are especially desirable. Furthermore, it is desirable that the hardness of the powdered silicone rubber used be a JIS A hardness of 80 or less, and a hardness of 65 or less is especially desirable. The reason for this is that cosmetics obtained by mixing a powdered silicone rubber whose JIS A hardness exceeds the abovementioned limit tend to be inadequate in terms of the feeling of said cosmetics during use. The conventional technical problem of cosmetics containing powdered silicone rubbers with low hardness values showing a good feeling during use, but presenting difficulties in terms of achieving a uniform dispersion of such powdered silicone rubbers in the cosmetics due to the large cohesive force of the powdered silicone rubbers themselves, is solved in a single stroke by the cosmetic raw material of the present invention.

It is desirable that the abovementioned aqueous suspension of a powdered silicone rubber be a suspension obtained by curing (for example) an addition reaction curable silicone rubber composition, a condensation reaction curable silicone rubber composition, an organic peroxide curable silicone rubber composition or an ultraviolet radiation curable silicone rubber composition in a state in which this composition is dispersed in water in the form of fine particles. Examples of such addition reaction curable silicone rubber compositions include compositions consisting of at least an organopolysiloxane which has at least two alkenyl groups per molecule, an organopolysiloxane which has at least two hydrogen atoms bonded to silicon atoms in each molecule, and a platinum type catalyst. Examples of condensation reaction curable silicone rubber compositions consisting of at least an organopolysiloxane which has at least two hydroxy groups or hydrolyzable groups such as alkoxy groups, oxime groups, acetoxy groups or aminoxy groups, etc., bonded to silicon atoms in each molecule, a silane cross-linking agent which has at least three hydrolyzable groups such as alkoxy groups, oxime groups, acetoxy groups or aminoxy groups, etc., bonded to silicon atoms in each molecule, and a condensation reaction catalyst such as an organo-tin compound or an organo-titanium compound, etc. In order to achieve a stable dispersion of these silicone rubber compositions as fine particles in water, it is desirable to use one or more nonionic surfactants, cationic surfactants and/or anionic surfactants. Since these surfactants are mixed with the cosmetic "as is", it is necessary to use surfactants that can be utilized as cosmetic raw materials. It is desirable that the amount of surfactant used be in the range of 0.1 to 20 parts by weight (preferably 0.5 to 10 parts by weight) per 100 parts by weight of the silicone rubber composition.

Furthermore, by using an aqueous suspension of a powdered silicone rubber containing a non-cross-linked oil as the cosmetic raw material of the present invention, it is possible to obtain a considerable softening of the feeling of the resulting cosmetic on the fingers and skin, and to improve the cosmetic durability. Examples of methods which can be used to manufacture such an aqueous suspension include a method in which an oil which does not participate in the curing reaction of the silicone rubber composition is added to this composition beforehand, after which the composition is dispersed in water in the form of fine particles and cured, and a method in which an oil is added to the abovementioned aqueous suspension of a powdered silicone rubber, after which this oil is caused to impregnate the powdered silicone rubber wider agitation. The former method is preferable.

The abovementioned non-cross-linked oil is an oil which is simply contained in the abovementioned powdered silicone rubber and which is naturally exuded from this powder, furthermore, this oil is an oil which can be extracted by means of organic solvents. Examples of such oils include non-cross-linked silicone oils and non-cross-linked organic oils. Such silicone oils are silicone oils which do not participate in the curing reaction used to form the powdered silicone rubber; the molecular structure of the oil used may be linear, linear with some branching, cyclic or branched, and is preferably linear. Non-reactive silicone oils such as dimethylpolysiloxanes which are closed by trimethylsiloxy groups at both ends of the molecular chains, dimethylsiloxane-methylphenylsiloxane copolymers which are closed by trimethylsiloxy groups at both ends of the molecular chains, and dimethylsiloxane-methyl(3,3,3-trifluoropropyl)siloxane copolymers which are closed by trimethylsiloxy groups at both ends of the molecular chains, etc., may generally be cited as examples of such silicone oils. For example, in cases where the abovementioned silicone oil is included beforehand in the silicone rubber composition which is used to form the powdered silicone rubber, dimethylpolysiloxanes closed by trimethylsiloxy groups at both ends of the molecular chains (which do not participate in the curing reaction), or polysiloxanes in which some of the methyl groups of such dimethylpolysiloxanes are replaced by alkyl groups other than methyl groups, or other groups such as phenyl groups or 3,3,3-trifluoropropyl groups, may be cited as examples in addition to the abovementioned non-reactive silicone oils. Furthermore, in cases where the curing reaction is an addition reaction, silicone oils such as dimethylpolysiloxanes which are closed by silanol groups at both ends of the molecular chains, or polysiloxanes in which some of the methyl groups of such dimethylpolysiloxanes are replaced by alkyl groups other than methyl groups, or other groups such as phenyl groups or 3,3,3-trifluoropropyl groups, etc., may be cited as examples in addition to the abovementioned non-reactive silicone oils. In addition, silicone oils which can participate in the curing reaction, but which remain unreacted, such as dimethylpolysiloxanes which are closed by dimethylvinylsiloxy groups at both ends of the molecular chains, dimethylsiloxane-methylvinylsiloxane copolymers which are closed by trimethylsiloxy groups at both ends of the molecular chains, dimethylpolysiloxanes which are closed by dimethylhydridosiloxy groups at both ends of the molecular chains, dimethylsiloxane-methylhydridosiloxane copolymers which are closed by trimethylsiloxy groups at both ends of the molecular chains, or polysiloxanes in which some of the methyl groups of such polysiloxanes are replaced by alkyl groups other than methyl groups, or other groups such as phenyl groups or 3,3,3-trifluoropropyl groups, etc., may also be cited as examples. Furthermore, in cases where the curing reaction is a condensation reaction, silicone oils such as polysiloxanes in which some of the methyl groups of the abovementioned non-reactive silicone oils are replaced by alkenyl groups, etc., may be cited as examples in addition to the abovementioned non-reactive silicone oils. Moreover, silicone oils which can participate in the curing reaction, but which remain unreacted, such as dimethylpolysiloxanes which are closed by silanol groups at both ends of the molecular chains, or silicone oils in which some of the methyl groups of such polysiloxanes are replaced by alkyl groups other than methyl groups, or other groups such as alkenyl groups, phenyl groups or 3,3,3-trifluoropropyl groups, may also be cited. Furthermore, in cases where the cured powdered silicone rubber is impregnated with a non-cross-linked silicone oil afterward, there are no restrictions on the type of silicone oil used.

Furthermore, examples of non-cross-linked organic oils which can be used include organic oils such as liquid paraffin, isoparaffin, hexyl laurate, isopropyl myristate, myristyl myristate, cetyl myristate, 2-octyldodecyl myristate, isopropyl palmitate, 2-ethylhexyl palmitate, butyl stearate, decyl oleate, 2-octyldodecyl oleate, myristyl lactate, cetyl lactate, lanolin lactate, stearyl alcohol, cetostearyl alcohol, oleyl alcohol, avocado oil, almond oil, olive oil, cacao oil, jojoba oil, sesame oil, safflower oil, soybean oil, camellia oil, squalene, persic oil, castor oil, mink oil, cottonseed oil, palm oil, egg yolk oil, beef tallow, lard, glycol ester oils such as polypropylene glycol monooleates and neopentyl glycol 2-ethylhexanoate, etc., polyhydric alcohol ester oils such as isostearic acid triglycerides and palm oil fatty acid triglycerides, etc., and polyoxyalkylene ether oils such as polyoxyethylene lauryl ethers and polyoxypropylene cetyl ethers, etc.

It is desirable that the abovementioned non-cross-linked oils be liquid in form, and that these oils have a viscosity of 100,000 mPaxs or less at 25° C. (a viscosity of 50,000 mPaxs is even more desirable, and a viscosity of 10,000 mPaxs or less is especially desirable. The reason for this is that in cases where an oil whose viscosity exceeds the abovementioned limit is used, it tends to become difficult to form a powdered silicone rubber whose mean particle size is less than 500 microns; furthermore, it tends to become difficult to impregnate the powdered silicone rubber with such an oil. Since the abovementioned non-cross-linked oils have a superior affinity for powdered silicone rubbers, it is desirable to use these oils.

It is desirable that the content of the abovementioned non-cross-linked oil in the powdered silicone rubber be 80 wt % or less, and a content of 50 wt % or less is especially desirable. The reason for this is that it is difficult to prepare a powdered silicone rubber whose non-cross-linked oil content exceeds the abovementioned limit, and there is a danger that cosmetics obtained using such a powdered silicone rubber will be sticky.

Furthermore, an aqueous suspension of a powdered silicone rubber whose surface is covered by a fine inorganic powder shows good stability as the cosmetic raw material of the present invention. One example of a method for preparing such an aqueous suspension is a method in which a fine inorganic powder is added to an aqueous suspension of a powdered silicone rubber, and the surface of the powdered silicone rubber is coated with this fine inorganic powder under agitation.

Examples of fine inorganic powders which can be used to cover the surface of the abovementioned powdered silicone rubber include fine powders of metal oxides such as silicon oxide, titanium oxide, zinc oxide, aluminum oxide, zirconium oxide or antimony oxide, etc., fine powders of metal nitrides such as boron nitride or aluminum nitride, etc., and fine powders of sulfides or fine powders of chloride, etc. Preferably, the fine powder used is a fine powder of a metal oxide; silicon oxide, titanium oxide and zinc oxide are especially desirable from the standpoint of good dispersibility of the powdered silicone rubber obtained and endowment of this powdered silicone rubber with the capacity to absorb ultraviolet radiation. These fine inorganic powders can be used "as is", or the surfaces of these powders can be treated beforehand with silicone, metal soaps, N-acylglutamic acid or fluorine. In regard to the mean particle size of these fine inorganic powders, a mean particle size which is sufficient to cover the surface of the powdered silicone rubber is acceptable. In concrete terms, a particle size which is 1/10 the mean particle size of the powdered silicone rubber or less is desirable, and it is also desirable that the specific surface area of this fine inorganic powder be 10 $m^2$ or greater.

The amount of fine inorganic powder that is added to the abovementioned aqueous suspension of a powdered silicone rubber is preferably in the range of 0.1 to 50 parts by weight (and even more preferably in the range of 1 to 20 parts by weight) per 100 parts by weight of powdered silicone rubber. The reason for this is as follows: i.e., if the amount of fine inorganic powder added per 100 parts by weight of the powdered silicone rubber is less than the lower limit of the abovementioned range, the surface of the powdered silicone rubber obtained cannot be covered by a sufficient amount of fine inorganic powder; on the other hand, if the amount exceeds the upper limit of the abovementioned range, the amount of fine inorganic powder which is not used to cover the surface of the powdered silicone rubber is increased.

There are no restrictions on the content of the powdered silicone rubber in the abovementioned aqueous suspension; however, it is desirable that this content be in the range of 10 to 80 wt % of the aqueous suspension. The reason for this is as follows: namely, if the powdered silicone rubber content of the aqueous suspension is lower than the abovementioned upper limit, the resulting cosmetic raw material lacks all-purpose characteristics, making it necessary in some cases to remove excess moisture in the manufacture of cosmetics. On the other hand, if the powdered silicone rubber content of the aqueous suspension exceeds the abovementioned upper limit, stable manufacture of such a suspension becomes difficult.

Next, the cosmetic of the present invention will be described in detail. The cosmetic of the present invention is characterized by the fact that this cosmetic consists of the abovementioned cosmetic raw material and other cosmetic raw materials. Examples of such cosmetics include cosmetics used for washing such as soaps, body shampoos and cleansing cremes, etc., basic cosmetics such as cosmetic lotions, cremes/emulsions and packs, etc., base makeup cosmetics such as powders and foundations, etc., lipsticks, rouge, eyebrow and eye cosmetics such as eye shadow, eye liner and mascara, etc., makeup cosmetics used in manicures, etc., hair-related cosmetics such as shampoos, hair rinses, hair conditioners, hair growth agents, hair nutrition agents and hair dyes, etc., fragrant cosmetics such as perfumes and eau de cologne, etc., toothpastes, bath preparations, and special cosmetics such as depilatory agents, shaving lotions, anti-perspirant/deodorant agents and sun screens, etc. Furthermore, examples of cosmetic formulations which can be used include aqueous liquid-form, oily liquid-form, emulsion-form, creme-form, foam-form, semi-solid, solid and powder-form formulations. Furthermore, such cosmetics may also be used in spray form.

The cosmetic of the present invention consists of [a] the abovementioned cosmetic raw material consisting of an aqueous suspension of a powdered silicone rubber, and [b] other cosmetic raw materials. Examples of such [other] cosmetic raw materials include fats and oils such as avocado oil, almond oil, olive oil, cacao oil, beef tallow, sesame oil, wheat germ oil, safflower oil, shia butter, turtle oil, camellia oil, persic oil, castor oil, grape oil, macadamia nut oil, mink oil, egg yolk oil, Japan wax, palm oil, rose hip oil and hardened oils, etc.; waxes such as orange roughy oil, carnauba wax, candelilla wax, ambergris, hohoba oil, montan wax, beeswax and lanolin, etc.; hydrocarbons such as liquid paraffin, vaseline, paraffin, ceresin, microcrystalline wax and squalene, etc.; higher fatty acids such as lauric acid, myristic acid, palmitic acid, stearic acid, oleic acid, behenic acid, undecylenic acid, oxystearic acid, linolic acid, lanolinic acid and synthetic fatty acids, etc.; alcohols such as ethyl alcohol, isopropyl alcohol, lauryl alcohol, cetyl alcohol, cetostearyl alcohol, stearyl alcohol, oleyl alcohol, behenyl alcohol, lanolin alcohol, hydrogenated lanolin alcohol, hexyldecanol, octyldodecanol and isostearyl alcohol, etc.; sterols such as cholesterol, dihydrocholesterol and phytosterol, etc.; fatty acid esters such as ethyl linolate, isopropyl myristate, isopropyl esters of lanolin fatty acids, hexyl laurate, myristyl myristate, cetyl myristate, octyldodecyl myristate, decyl oleate, octyldodecyl oleate, hexyldecyl dimethyloctanoate, cetyl isooctanoate, cetyl palmitate, glycerol trimyristate, glycerol tri(capryl-caprate), propylene glycol dioleate, glycerol triisostearate, glycerol triisooctanoate, cetyl lactate, myristyl lactate and diisostearyl malate, etc.; moisture-retaining agents such as glycerol, propylene glycol, 1,3-butylene glycol, polyethylene glycol, sodium d1-pyrrolidonecarboxylate, sodium lactate, sorbitol and sodium hyaluronate, etc.; surfactants, e.g., anionic surfactants such as higher fatty acid soaps, sulfuric acid esters of higher alcohols, N-acylglutarnates and phosphoric acid esters, etc., cationic surfactants, amphoteric surfactants such as betaine type, amino acid type, imidazoline type or lecithin type surfactants, etc., and nonionic surfactants such as polyhydric alcohol ester type and ethylene oxide condensation type surfactants, etc.; pigments, e.g., colored pigments such as iron oxide, etc., white pigments such as zinc oxide, titanium oxide and zirconium oxide, etc., and body pigments such as mica, talc and cerisite, etc.; silicone oils such as dimethylpolysiloxanes, methylphenylpolysiloxanes, octamethyltetracyclosiloxanes, decamethylcyclopentasiloxanes, polyether-modified silicone oils and amino-modified silicone oils, etc.; purified water; thickeners such as carrageenan, alginic acid, gum arabic, tranganth, pectin, starch, xanthan gum, polyvinyl alcohols, polyvinylpyrrolidones, sodium polyacrylate and polyethylene glycols, etc.; and other additives such as ultra-violet absorbing agents, anti-bacterial agents, anti-inflammatory agents, anti-perspirant agents, preservatives, fragrances, oxidation inhibitors, pH adjusting agents and spray agents, etc.

Next, the cosmetic manufacturing method of the present invention will be described in detail.

The manufacturing method of the present invention is characterized by the fact that the abovementioned cosmetic raw material consisting of an aqueous suspension of a powdered silicone rubber is mixed with the abovementioned other cosmetic raw materials. The method of the present invention makes it possible to disperse a powdered silicone rubber uniformly in cosmetic products, without any need for a special apparatus or a high shearing force. In the manufacturing method of the present invention, for example, cosmetics can be manufactured using either a batch system or a continuous system. Examples of apparatus types which can be used for this purpose include homo-mixers, paddle mixers, Henschel mixers, homo-dispersers, colloid mixers, propeller agitators, homogenizers, in-line continuous emulsifiers, ultrasonic emulsifiers and vacuum kneaders, etc. Furthermore, in the cosmetic of the present invention, moisture may be removed in the cosmetic manufacturing process in cases where water is unnecessary.

PRACTICAL EXAMPLES OF APPLICATION

The cosmetic raw material, cosmetic and cosmetic manufacturing method of the present invention will be described in detail in terms of practical examples of application. Furthermore, all viscosity values in the practical examples are values at 25° C.

Concerning the Cosmetic Raw Material

Examples of the cosmetic raw material of the present invention were prepared as described below. Furthermore, the mean particle size of the powdered silicone rubber [in each case] was determined by using an optical microscope linked to an image processing device to measure the mean particle size of the powdered silicone rubber obtained by removing the water from the powdered silicone rubber in the aqueous suspension.

Practical Example 1

A silicone rubber composition was prepared by uniformly mixing 96 parts by weight of a dimethylpolysiloxane closed by dimethylvinylsiloxy groups at both ends of the molecular chains (with a viscosity of 400 mPaxs), 4 parts by weight of a methylhydridopolysiloxane closed by trimethylsiloxy groups at both ends of the molecular chains (viscosity 20 mPaxs, content of hydrogen atoms bonded to silicon atoms= 1.5 wt %), 6 parts by weight of a dimethylpolysiloxane closed by trimethylsiloxy groups at both ends of the molecular chains (with a viscosity of 20 mPaxs) and an isopropyl alcohol solution of chloroplatinic acid (used in an amount which was such that the concentration of the platinum metal in this alcohol solution relative to the abovementioned dimethylpolysiloxane closed by dimethylvinylsiloxy groups at both ends of the molecular chains was 20 ppm). The JIS A hardness of the silicon rubber obtained by allowing this composition to stand for 1 day at room temperature was 28. Next, the total amount of this silicone rubber composition was emulsified using 53 parts by weight of a 3 wt % aqueous solution of a polyoxyethylene nonylphenyl ether (HLB= 13.1); afterward, 50 parts by weight of pure water was added, thus producing an aqueous emulsion of the abovementioned silicone rubber composition. The silicone rubber composition was cured by allowing the abovementioned aqueous emulsion to stand for 1 day at room temperature, thus producing an aqueous suspension of a powdered silicone rubber. This aqueous suspension was designated as cosmetic raw material (A). The shape of the silicone rubber powder particles was spherical, and the mean particle size of these particles was 4 microns. 100 parts by weight of this powdered silicone rubber was placed in a vessel; next, 1000 parts by weight of toluene was added, and this mixture was agitated for 10 minutes at 1000 rpm, and then for 30 minutes at 500 rpm, by means of a homodisperser (manufactured by Tokushuki Kako K.K.), after which the mixture was allowed to stand for 12 hours. Subsequently, the mixture was agitated for 10 minutes at 500 rpm by means of the aforementioned homo-disperser, and was then filtered by means of a sterilizing filtration device using a filter paper. The toluene was removed from the resulting filtrate by means of an evaporator, thus producing a non-cross-linked oil. The non-cross-linked oil content of the powdered silicone rubber was 6 wt %. This non-cross-linked oil was analyzed by means of a gel permeation chromatograph, infrared spectral analysis and $^1$H-nuclear magnetic resonance analysis; as a result, it was found that this non-cross-linked oil consisted mainly of a dimethylpolysiloxane closed by trimethylsiloxy groups at both ends of the molecular chains (with a viscosity of 20 mPaxs), and also contained other dimethylcyclopolysiloxanes.

Practical Example 2

2.5 parts by weight of fumed silica with a BET specific surface area of 200 m²/g was added to 100 parts by weight of an aqueous suspension of a powdered silicone rubber prepared in the same manner as in Practical Example 1, and this mixture was heated and agitated for 2 hours at 60° C., thus producing an aqueous suspension of a powdered silicone rubber whose particles surfaces were covered by fumed silica. A portion of this aqueous suspension was collected, and the powdered silicone rubber was separated. When this powdered silicone rubber was decomposed by means of a highly concentrated aqueous solution of potassium hydroxide, and the decomposition products were analyzed by gas chromatography, it was found that this powdered silicone rubber was covered by approximately 4 wt % fumed silica. Furthermore, the cured silicone rubber was shaken in isopropyl alcohol; however, no separation of fumed silica from the powdered silicone rubber was observed. This aqueous suspension was designated as cosmetic raw material (B).

Practical Example 3

A silicone rubber composition was prepared by uniformly mixing 96 parts by weight of a dimethylpolysiloxane closed by dimethylvinylsiloxy groups at both ends of the molecular chains (with a viscosity of 400 mPaxs), 3 parts by weight of a methylhydridosiloxane-dimethylsiloxane copolymer closed by trimethylsiloxy groups at both ends of the molecular chains (viscosity 20 mPaxs, content of hydrogen atoms bonded to silicon atoms=0.7 wt %) and an isopropyl alcohol solution of chloroplatinic acid (used in an amount which was such that the concentration of the platinum metal in this alcohol solution relative to the abovementioned dimethylpolysiloxane closed by dimethylvinylsiloxy groups at both ends of the molecular chains was 20 ppm). The JIS A hardness of the silicon rubber obtained by allowing this composition to stand for 1 day at room temperature was 31. Next, the total amount of this silicone rubber composition was emulsified using 50 parts by weight of a 3 wt % aqueous solution of a polyoxyethylene nonylphenyl ether (HLB= 13.1), thus producing an aqueous emulsion of the abovementioned silicone rubber composition. The silicone rubber composition was cured by allowing the abovementioned aqueous emulsion to stand for 1 day at room temperature, thus producing an aqueous suspension of a powdered silicone rubber. The shape of the silicone rubber powder particles was spherical, and the mean particle size of these particles was 4 microns. This aqueous suspension was designated as cosmetic raw material ©.

Reference Example 1

A powdered silicone rubber was prepared by spraying an aqueous suspension of a powdered silicone rubber prepared in the same manner as in Practical Example 1 into a hot air draft at 300° C. so that the water content was removed. This powdered silicone rubber was designated as cosmetic raw material (D).

Concerning the Cosmetic Manufacturing Method and Cosmetic

Examples of the cosmetic of the present invention were prepared as described below. Furthermore, the feeling of the cosmetic in each case, and the state of dispersion of the powdered silicone rubber in the cosmetic, were evaluated as follows:

Feeling of the Cosmetic on the Fingers

Each cosmetic was used by 10 panelists. In cases where the number of panelists who reported that the feeling of the cosmetic was good was 8 to 10 panelists, the cosmetic was graded with a "circle"; in cases where this number of panelists was 4 to 7 panelists, the cosmetic was graded with a "triangle", and in cases where this number of panelists was 3 panelists or fewer, the cosmetic was graded with an "X".

Feeling of the Cosmetic on the Skin

Each cosmetic was used by 10 panelists. In cases where the number of panelists who reported that the feeling of the cosmetic was good was 8 to 10 panelists, the cosmetic was graded with a "circle"; in cases where this number of panelists was 4 to 7 panelists, the cosmetic was graded with a "triangle", and in cases where this number of panelists was 3 panelists or fewer, the cosmetic was graded with an "X".

State of Dispersion of the Powdered Silicon Rubber in the Cosmetic

Each cosmetic was thinly spread on a glass plate, and the particle size [distribution] of the powdered silicone rubber in the cosmetic was observed using an optical microscope. The proportion of the powdered silicone resin showing a particle size of 10 microns or less, the proportion of the powdered silicone resin showing a particle size exceeding 10 microns but not exceeding 50 microns, and the proportion of the powdered silicone resin showing a particle size exceeding 50 microns, were respectively determined, and the dispersibility of the powdered silicone rubber in the cosmetic was evaluated in this way.

Practical Example 4

52 parts by weight of cosmetic raw material (A), 5 parts by weight of octyl p-methoxycinnamate, 1 part by weight of a-monoisostearylglyceryl ether polyoxyethylene sorbitan monooleic acid ester, 2 parts by weight of beeswax, 2 parts by weight of lanolin, 10 parts by weight of squalene, 10 parts by weight of liquid paraffin, 19 parts by weight of purified water, an appropriate amount of a preservative and an appropriate amount of a fragrance were agitated for 5 minutes at 2500 rpm by means of a homo-disperser, thus producing an emulsion-form cosmetic. The evaluation results obtained for this cosmetic are shown in Table 1.

Practical Example 5

52 parts by weight of cosmetic raw material (B), 5 parts by weight of octyl p-methoxycinnamate, 1 part by weight of a-monoisostearylglyceryl ether polyoxyethylene sorbitan monooleic acid ester, 2 parts by weight of beeswax, 2 parts by weight of lanolin, 10 parts by weight of squalene, 10 parts by weight of liquid paraffin, 19 parts by weight of purified water, an appropriate amount of a preservative and an appropriate amount of a fragrance were agitated for 5 minutes at 2500 rpm by means of a homo-disperser, thus producing an emulsion-form cosmetic. The evaluation results obtained for this cosmetic are shown in Table 1.

Comparative Example 1

24 parts by weight of cosmetic raw material (D), 5 parts by weight of octyl p-methoxycinnamate, 1 part by weight of a-monoisostearylglyceryl ether polyoxyethylene sorbitan monooleic acid ester, 2 parts by weight of beeswax, 2 parts by weight of lanolin, 10 parts by weight of squalene, 10 parts by weight of liquid paraffin, 45 parts by weight of purified water, an appropriate amount of a preservative and an appropriate amount of a fragrance were agitated for 5 minutes at 2500 rpm by means of a homo-disperser, thus producing an emulsion-form cosmetic. The evaluation results obtained for this cosmetic are shown in Table 1.

TABLE 1

| Sample Item | distinction | Practical Example 4 | Practical Example 5 | Comparative Comparative Example 1 |
|---|---|---|---|---|
| Feeling on fingers | | ○ | ○ | ○ |
| Feeling on skin | | ○ | ○ | Δ Grainy feeling present |
| State of dispersion (particle size) of powdered silicone rubber in cosmetic | | | | |
| ≦10 µm | | 100% | 100% | 0% |
| 10 µm<, ≦50 µm | | 0% | 0% | 100% |
| 50 µm< | | 0% | 0% | 0% |

Practical Example 6

40 parts by weight of cosmetic raw material ©, 1 part by weight of silicone-treated titanium oxide, 5 parts by weight of octyl p-methoxycinnamate, 10 parts by weight of a dimethylpolysiloxane closed by trimethylsiloxy groups at both ends of the molecular chains (with a viscosity of 20 mPaxs), 3 parts by weight of polyoxyethylene (40 mol adduct) hardened castor oil, 30 parts by weight of squalene, 5 parts by weight of glycerol, 3 parts by weight of beeswax, an appropriate amount of a preservative, an appropriate amount of a fragrance and an appropriate amount of purified water were agitated for 10 minutes at 1500 rpm by means of a Henschel mixer, thus producing a creme-form cosmetic. The evaluation results obtained for this cosmetic are shown in Table 2.

Comparative Example 2

20 parts by weight of cosmetic raw material (D), 1 part by weight of silicone-treated titanium oxide, 5 parts by weight of octyl p-methoxycinnamate, 10 parts by weight of a dimethylpolysiloxane closed by trimethylsiloxy groups at both ends of the molecular chains (with a viscosity of 20 mPaxs), 3 parts by weight of polyoxyethylene (40 mol adduct) hardened castor oil, 30 parts by weight of squalene, 5 parts by weight of glycerol, 3 parts by weight of beeswax, an appropriate amount of a preservative, an appropriate amount of a fragrance and an appropriate amount of purified water were agitated for 10 minutes at 1500 rpm by means of a Henschel mixer, thus producing a creme-form cosmetic. The evaluation results obtained for this cosmetic are shown in Table 2.

TABLE 2

| Sample Item | distinction | Present invention Practical Example 6 | Comparative example Comparative Example 2 |
|---|---|---|---|
| Feeling on fingers | | ○ | Δ |
| | | ○ | Heavy feeling |
| Feeling on skin | | ○ | Δ |
| | | ○ | Grainy feeling present |
| Sate of dispersion (particle size) of powdered silicone rubber in cosmetic | | | |
| | ≦10 μm | 100% | 40% |
| | 10 μm<, <50 μm | 0% | 50% |
| | 50 μm < | 0% | 10% |

Practical Example 7

14 parts by weight of cosmetic raw material (A), 2 parts by weight of 1,3-butylene glycol, 50 parts by weight of ethanol, 1 part by weight of a polyether-modified silicone oil (SH3771 manufactured by Toray—Dow Corning—Silicone K.K.), 4 parts by weight of propylene glycol, 1 part by weight of polyoxyethylene (15 mol adduct) nonyl ether, 1 part by weight of silicone-treated titanium oxide, an appropriate amount of a preservative, an appropriate amount of a fragrance and an appropriate amount of purified water were agitated for 10 minutes at 1500 rpm by means of a Henschel mixer, thus producing an aqueous cosmetic. The evaluation results obtained for this cosmetic are shown in Table 3.

Comparative Example 3

7 parts by weight of cosmetic raw material (D), 2 parts by weight of 1,3-butylene glycol, 50 parts by weight of ethanol, 1 part by weight of a polyether-modified silicone oil (SH3771 manufactured by Toray—Dow Corning—Silicone K.K.), 4 parts by weight of propylene glycol, 1 part by weight of polyoxyethylene (15 mol adduct) nonyl ether, 1 part by weight of silicone-treated titanium oxide, an appropriate amount of a preservative, an appropriate amount of a fragrance and an appropriate amount of purified water were agitated for 10 minutes at 1500 rpm by means of a Henschel mixer, thus producing an aqueous cosmetic. The evaluation results obtained for this cosmetic are shown in Table 3.

TABLE 3

| Sample Item | distinction | Present invention Practical Example 7 | Comparative example Comparative Example 3 |
|---|---|---|---|
| Feeling on fingers | | ○ | Δ |
| | | ○ | Heavy feeling |
| Feeling on skin | | ○ | Δ |
| | | ○ | Grainy feeling present |
| State of dispersion (particle size) of powdered silicone rubber in cosmetic | | | |
| | <10 μm | 100% | 30% |
| | 10 μm<, ≦50 μm | 0% | 30% |
| | 50 μm< | 0% | 40% |

Merits of the Invention

The cosmetic raw material of the present invention is characterized by the fact that said cosmetic raw material allows the uniform dispersion of a powdered silicone rubber in a cosmetic. Furthermore, the cosmetic of the present invention consists of the abovementioned cosmetic raw material and other cosmetic raw materials, and is characterized by the fact that said cosmetic contains a uniformly dispersed powdered silicone rubber, and has a good feeling on the fingers and skin, good spreading characteristics, and a good feeling during use. Moreover, the cosmetic manufacturing method of the present invention is characterized by the fact that said method makes it possible to manufacture such a cosmetic with good efficiency.

We claim:

1. A cosmetic raw material consisting of an aqueous suspension of a powdered silicone rubber with a mean particle size of 0.1 to 500 microns, the aqueous suspension of powdered silicone rubber being obtained by curing a silicon rubber composition dispersed in water in the form of fine particles containing a non-crosslinked oil.

2. The cosmetic raw material claimed in claim 1, which is characterized by the fact that the aforementioned powdered silicone rubber contains a non-cross-linked oil.

3. The cosmetic raw material claimed in claim 1, which is characterized by the fact that the surface of the aforementioned powdered silicone rubber is covered by a fine inorganic powder.

4. A cosmetic which is characterized by the fact that said cosmetic consists of the cosmetic raw material in claim 1, and other cosmetic raw materials.

5. A method for manufacturing the cosmetic claimed in claim 4, which is characterized by the fact that the cosmetic raw material of claim 1 is mixed with other cosmetic raw materials.

6. A cosmetic comprising a composition manufactured by (I) mixing:

(A) an aqueous suspension of a powdered silicone rubber with a mean particle size of 0.1 to 500 microns, the aqueous suspension of powdered silicone rubber being obtained by curing a silicon rubber composition dispersed in water in the form of fine particles, the powdered silicone rubber containing a non-cross-linked oil, and the surface of the powdered silicone rubber being covered by a fine inorganic powder; and (B) a cosmetic material selected from the group consisting of fats, oils, waxes, hydrocarbons, higher fatty acids, alcohols, sterols, fatty acid esters, moisture retaining agents, surfactants, pigments, silicone oils, thickeners, ultraviolet absorbing agents, antibacterial agents, anti-inflammatory agents, antiperspirant agents, preservatives, fragrances, oxidation inhibitors, pH adjusting agents, and spray agents;

and (II) removing moisture from the composition during manufacture of the cosmetic.

* * * * *